US012702301B2

(12) United States Patent
Yu

(10) Patent No.: US 12,702,301 B2
(45) **Date of Patent: *Aug. 11, 2026**

(54) SYSTEM AND METHOD FOR ASSESSMENT OF NEURO-INFLAMMATION USING MAGNETIC RESONANCE IMAGING (MRI)

(71) Applicant: Wisconsin Alumni Research Foundation, Madison, WI (US)

(72) Inventor: John-Paul Jaewoon Yu, Madison, WI (US)

(73) Assignee: Wisconsin Alumni Research Foundation, Madison, WI (US)

(*) Notice: Subject to any disclaimer, the term of this patent is extended or adjusted under 35 U.S.C. 154(b) by 0 days.

This patent is subject to a terminal disclaimer.

(21) Appl. No.: 19/073,911

(22) Filed: Mar. 7, 2025

(65) Prior Publication Data

US 2025/0204783 A1 Jun. 26, 2025

Related U.S. Application Data

(63) Continuation of application No. 16/421,311, filed on May 23, 2019, now Pat. No. 12,268,466.

(Continued)

(51) Int. Cl.
*A61B 5/00* (2006.01)
*A61B 5/055* (2006.01)

(Continued)

(52) U.S. Cl.
CPC ............ *A61B 5/0042* (2013.01); *A61B 5/055* (2013.01); *G01R 33/5608* (2013.01); *G01R 33/56341* (2013.01); *A61B 2576/026* (2013.01)

(58) Field of Classification Search
CPC . A61B 5/0042; A61B 5/055; A61B 2576/026; G01R 33/5608; G01R 33/56341
See application file for complete search history.

(56) References Cited

U.S. PATENT DOCUMENTS

| | | | |
|---|---|---|---|
| 2016/0187443 | A1 | 6/2016 | Liu |
| 2016/0231410 | A1 | 8/2016 | Warfield |

(Continued)

OTHER PUBLICATIONS

Assaf, Y., et al (2005). Composite hindered and restricted model of diffusion (Charmed) MR imaging of the human brain. NeuroImage 27, 48-58. doi: 10.1016/j.neuroimage.2005.03.042.

(Continued)

*Primary Examiner* — Keith M Raymond
*Assistant Examiner* — Adam D. Kolkin
(74) *Attorney, Agent, or Firm* — Quarles & Brady LLP

(57) ABSTRACT

A system and method are provided for non-invasively assessing neuro-inflammation in a subject. The method includes acquiring neurite orientation dispersion and density imaging (NODDI) data of the subject and processing the NODDI data to determine an orientation dispersion index (ODI) component of the NODDI data. The method also includes assessing the ODI component against one of a reference of neuro-inflammation or a prior ODI component acquired from the subject to determine one of an acute assessment or a chronic assessment of neuro-inflammation in the subject. The method further includes generating a report indicating the one of an acute assessment or a chronic assessment of neuro-inflammation in the subject.

20 Claims, 7 Drawing Sheets

Related U.S. Application Data

(60) Provisional application No. 62/677,295, filed on May 29, 2018.

(51) Int. Cl.
*G01R 33/56* (2006.01)
*G01R 33/563* (2006.01)

(56) References Cited

U.S. PATENT DOCUMENTS

2016/0334489 A1* 11/2016 Sperl .................. G01R 33/5608
2016/0343129 A1 11/2016 Novikov
2018/0116603 A1 5/2018 Alexander
2018/0263569 A1* 9/2018 Wang ................... A61B 5/7275

OTHER PUBLICATIONS

Assaf, Y., et al (2008). AxCaliber: a method for measuring axon diameter distribution from diffusion MRI. Magn. Reson. Med. 59, 1347-1354. doi: 10.1002/mrm.21577.
Alexander, D. C., et al. (2010). Orientationally invariant indices of axon diameter and density from diffusion MRI. NeuroImage 52, 1374-1389. doi: 10.1016/j.neuroimage.2010.05.043.
Colgan, N. et al., Application of neurite orientation dispersion and density imaging (NODDI) to a tau pathology model of Alzheimer's disease. Neuroimage. 125, 739-744 (2016).
Grussu, F., et al. (2017). Neurite dispersion: a new marker of multiple sclerosis spinal cord pathology? Ann. Clin. Transl. Neurol. 663-79. doi: 10.1002/acn3.445.
Grussu, F., et al., Neurite orientation dispersion and density imaging of the healthy cervical spinal cord in vivo. Neuroimage. 111, 590-601 (2015).
Harms, R. L., et al. (2017). Robust and fast nonlinear optimization of Di Ff Usion MRI microstructure models. NeuroImage 155:82-96. doi: 10.1016/j.neuroimage.2017.04.064.
Harrison N.A. et al., Quantitative Magnetization Transfer Imaging as a Biomarker for Effects of Systemic Inflammation on the Brain. Biol. Psychiatry. 78, 49-57 (2015).
Slattery, Catherine F. et al. Music as a Probe of Default Mode Network Function in Young-Onset Alzheimer's Disease, Alzheimer's & Dementia: The Journal of the Alzheimer's Association , vol. 11, Issue 7 , p. 91, Jul. 2015.
Stoll, G., et al., Imaging of inflammation in the peripheral and central nervous system by magnetic resonance imaging. Neuroscience. 158, 1151-1160 (2009).
Tariq, M., et al., Bingham-•NODDI: Mapping anisotropic orientation dispersion of neurites using diffusion MRI. Neuroimage. 133, 207-223 (2016).
Streit, W. J., et al. (2004). Microglia and neuroinflammation: a pathological perspective. Journal of neuroinflammation, 1 (1), 1-4 ( Year: 2004).
Zhang, H., Schneider, T., Wheeler-Kingshott, C., & Alexander, D. C., NODDI: Practical in vivo neurite orientation dispersion and density imaging of the human brain, 2012, NeuroImage, 61 (4), 1000-1016. (Year: 2012).
Caverzasi, E., et al. (2016). Neurite orientation dispersion and density imaging color maps to characterize brain diffusion in neurologic disorders. Journal of Neuroimaging, 26(5), 494-498 (Year: 2016).
Adluru, Ganesh et al. "Assessment of white matter microstructure in stroke patients using NODDI." Annual International Conference of the IEEE Engineering in Medicine and Biology Society. IEEE Engineering in Medicine and Biology Society. Annual International Conference vol. 2014 (2014): 742-5. (Year: 2014).
Churchill, Nathan Wet al. "White matter microstructure in athletes with a history of concussion: Comparing diffusion tensor imaging (DTI) and neurite orientation dispersion and density imaging (NODDI)." Human brain mapping vol. 38,8 (2017): 4201-4211. (Year: 2017).
Schneider, Torben et al. "Sensitivity of multi-shell NODDI to multiple sclerosis white matter changes: a pilot study." Functional neurology vol. 32,2 (2017): 97-101. (Year: 2017).
Crombe, Amandine et al. "Deciphering the microstructure of hippocampal subfields with in vivo DTI and NODDI: Applications to experimental multiple sclerosis." NeuroImage vol. 172 (2018): 357-368. (Year: 2018).
Parker, Thomas D et al. "Cortical microstructure in young onset Alzheimer's disease using neurite orientation dispersion and density imaging." Human brain mapping vol. 39,7 (2018): 3005-3017. (Year: 2018).
Rodrfguez, JJ, et al., Increase in the Density of Resting Microglia Precedes Neuritic Plaque Formation and Microglial Activation in a Transgenic Model of Alzheimer's Disease, Jan. 14, 2010, Cell Death and Disease, 1. (Year: 2010).
Hammond, C., Cellular and Molecular Neurobiology, 2012, Burlington: Elsevier Science, 2nd Ed., 24. (Year: 2012).
Morales, Inelia, et al., Tau Oligomers and Fibrils Induce Activation of Microglial Cells, 2013, Journal of Alzheimer's Disease 37, 851-55. (Year: 2013).
Zhang, F. & Jiang, L, Neuroinflammation in Alzheimer's Disease, 2015, Neuropsychiatric Disease and Treatment, 11, 243. (Year: 2015).
Mayer, A. R., Ling, J.M., Dodd, A. B., Meier, T. B., Hanlon, F. M., & Klimaj, S. D., A prospective microstructure imaging study in mixed-martial artists using geometric measures and diffusion tensor imaging: Methods and findings. Brain Imaging and Behavior, 2017, 11 (3), 698-711. (Year: 2017).

* cited by examiner 100
136
OPERATOR WORKSTATION
102
104
106
108
NETWORKED WORKSTATION
142
144
146
148
138
DATA STORE SERVER
116
GRADIENT SYSTEM
118
PULSE SEQUENCE SERVER
110
DATA ACQUISITION SERVER
112
DATA PROCESSING SERVER
114
COMMUNICATION SYSTEM
140
PHYSIOLOGICAL ACQUISITION CONTROLLER
130
SCAN ROOM INTERFACE
132
RF SYSTEM
120
PATIENT POSITIONING SYSTEM
134
124
122
126
128

SYSTEM AND METHOD FOR ASSESSMENT OF NEURO-INFLAMMATION USING MAGNETIC RESONANCE IMAGING (MRI)

CROSS REFERENCE TO RELATED APPLICATIONS

This application is a continuation of U.S. application Ser. No. 16/421,311, filed May 23, 2019, which application is based, claims priority to, and incorporates hereby reference in its entirety U.S. Provisional Application Ser. No. 62/677,295, filed May 29, 2018, and entitled, "SYSTEM AND METHOD FOR ASSESSMENT OF NEURO-INFLAMMATION USING MAGNETIC RESONANCE IMAGING (MRI)."

STATEMENT REGARDING FEDERALLY SPONSORED RESEARCH

N/A

BACKGROUND

The field of the invention is systems and methods for magnetic resonance imaging ("MRI"). More particularly, the invention relates to systems and methods for using MRI to assess neuro-inflammation.

Brain-immune interactions contribute to numerous acute and chronic disorders of the central nervous system (CNS) from ischemic stroke and traumatic brain injury to age-related dementia and Alzheimer's disease. Schizophrenia, major depression, and other neuropsychiatric disorders also exhibit hallmarks of neuro-inflammation, where peripheral cellular and humoral immunological abnormalities are more prevalent in psychiatric patients than in healthy controls. Genome-wide studies in schizophrenia have also revealed an association with markers in the major histocompatibility complex region (MHC) and post-mortem studies have provided evidence of increased microglial populations and microglial activation in patients with schizophrenia, depression, and other affective disorders. With a growing recognition of the role that microglial-mediated neuro-inflammation plays in the neuropath genesis of psychiatric disorders, there is significant interest in the development of new methodologies aimed at assessing neuro-inflammation, microglial populations, and their distribution throughout the brain.

Microglia are parenchymal tissue macrophages of the central nervous system (CNS) that are derived from macrophages produced by primitive hematopoiesis in the yolk sac. These primitive macrophages subsequently migrate to the neural tube during development and give rise to the mature microglial pool without contributions from peripheral marrow-derived monocytes. Comprising approximately 5 to 15% of the total number of cells in the CNS, microglia are highly dynamic glial cells capable of remarkable fluctuations in their total cell population. Microglia serve as the first line of defense against tissue damage and infection by pathogen recognition, phagocytosis, and antigen recognition and, in addition, express and release of pro-inflammatory mediators and other signaling molecules. Microglial-mediated neuro-inflammation has been implicated across a broad range of acute and chronic neurologic disorders including ischemic stroke, traumatic brain injury, epilepsy, and chronic neurodegenerative disorders, such as Alzheimer's disease and Parkinson's disease. Numerous neuropsychiatric disorders including schizophrenia, major depression, and autism spectrum disorder have also been shown to exhibit hallmarks of neuro-inflammation, where peripheral cellular and humoral immunological abnormalities are more prevalent in psychiatric patients than in healthy controls.

Genome-wide studies in schizophrenia have also revealed an association with markers in the major histocompatibility complex region (MHC) and post-mortem studies have provided evidence of increased microglial populations and microglial activation in patients with schizophrenia, depression, and other affective disorders.

Numerous neuroimaging techniques have been developed in an attempt to characterize neuro-inflammatory processes in vivo. These techniques generally fall into two major methodological categories. The first category is nuclear imaging, such as positron emission tomography (PET) and single photon emission computed tomography (SPECT). The second category is magnetic resonance imaging (MRI).

Nuclear imaging methods have principally focused on the imaging of resident immunocompetent cells, specifically targeting activated microglia with translocator protein (TSPO) PET imaging. TSPO is a 18 kD five transmembrane domain protein that is constitutively expressed at low levels by numerous cells types in the CNS. However, under inflammatory conditions, TSPO is substantially upregulated in microglia and astrocytes lending itself as an attractive target for PET imaging studies aimed at imaging glial activation and neuro-inflammation. Since the 1980s with the initial synthesis of $^{11}$C-PK11195, a series of second and now third generation TSPO ligands have been produced including $^{11}$C-PBR28, $^{18}$F-DPA-714, and $^{18}$F-GE180. Despite higher affinities and improved binding profiles, there are significant challenges to quantification, including (1) polymorphisms of the TSPO gene, (2) complex tracer kinetics due to heterogeneity of TSPO distribution in brain tissue, and (3) variability of plasma free fractions across human clinical cohorts, which have been evident in recent clinical trials investigating TSPO imaging in schizophrenia.

In contradistinction to nuclear imaging, magnetic resonance imaging of neuro-inflammation faces significant challenges related to specificity. Techniques such as magnetic resonance (MR) diffusion tensor imaging (DTI) are hampered by a lack of specificity in scalar measures of the diffusion tensor, which may be sensitive to neuro-inflammation, but also to many other changes in tissue geometry that can occur such as demyelination, changes in the organization of fibers, partial volume effects, and membrane permeability. Similarly, other MR techniques such as magnetization transfer (MT) imaging are also hampered by a lack of specificity with myelin content and parenchymal edema confounding the magnetization transfer ratio (MTR). Cellular magnetic resonance imaging techniques have also been developed employing the use of iron oxide contrast agents (small (SPIO) and ultra-small (USPIO) particles of iron oxide) that are preferentially phagocytosed by circulating monocytes. These SPIOs and USPIOs produce substantial shortening of both T1- and T2-relaxation times (greater than that of gadolinium-based contrast agents); thus, enabling visualization of iron-laden cells tracking to inflammatory tissue at clinical field strengths. The extent to which circulating monocytes cross the blood-brain barrier (BBB) remains controversial, in addition to other concerns regarding the biocompatibility and toxicity of SPIOs and USPIOs. Overall, despite active research efforts to image central nervous system neuro-inflammation, there remains no safe, accurate, widely accessible, or clinically viable neuroimaging methodology available for the in vivo study of neuro-inflammation.

Thus, it would be desirable to have a system and method for non-invasive, quantitative assessment neuro-inflammation.

SUMMARY

The present disclosure overcomes the aforementioned drawbacks by providing systems and methods for assessing neuro-inflammation using an advanced, multi-compartment diffusion MRI methodology to detect changes in microglial density and morphology in acute and chronic microglial activation. The systems and methods provided herein can assess the distribution and density of microglial populations to image and assess a neuroimaging biomarker of neuro-inflammation. More particularly, the systems and methods provided herein recognize that neurite orientation dispersion and density imaging (NODDI) is sensitive to changes in microglial density that are associated with neuro-inflammation. Thus, a system and method is provided that utilizes the NODDI to distinguish the extracellular space (ODI; orientation dispersion index, inclusive of microglia) as a unique and quantitative microstructural environment and generate a quantitative parametric measure of NODDI to provide quantitative and clinically applicable assessments of neuro-inflammation, as well as indications of longitudinal neuro-inflammation.

In accordance with one aspect of the disclosure, a magnetic resonance imaging (MRI) system is provided that includes a magnet system configured to generate a polarizing magnetic field about at least a portion of a subject arranged in the MRI system. The MRI system also includes a plurality of gradient coils configured to apply a gradient field to the polarizing magnetic field and a radio frequency (RF) system configured to apply an excitation field to the subject and acquire MR image data from the subject. The MRI system further includes a computer system programmed to control the plurality of gradient coils and the RF system to acquire neurite orientation dispersion and density imaging (NODDI) data from the subject. The computer system is further programmed to process the NODDI data to determine an orientation dispersion index (ODI) component of the NODDI data and assess the ODI component against one of a reference of neuro-inflammation or a prior ODI component acquired from the subject to determine one of an acute assessment or a chronic assessment of neuro-inflammation in the subject. The computer system is further programmed to generate a report indicating the one of an acute assessment or a chronic assessment of neuro-inflammation in the subject.

In accordance with another aspect of the disclosure, a method is provided for non-invasively assessing neuro-inflammation in a subject. The method includes acquiring neurite orientation dispersion and density imaging (NODDI) data of the subject and processing the NODDI data to determine an orientation dispersion index (ODI) component of the NODDI data. The method also includes assessing the ODI component against one of a reference of neuro-inflammation or a prior ODI component acquired from the subject to determine one of an acute assessment or a chronic assessment of neuro-inflammation in the subject. The method further includes generating a report indicating the one of an acute assessment or a chronic assessment of neuro-inflammation in the subject The foregoing and other aspects and advantages of the invention will appear from the following description. In the description, reference is made to the accompanying drawings, which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION

As described above, current methodologies for assessments of inflammation are encumbered by significant limitations including low specificity, inability to accurately quantify, and low biocompatibility/toxicity. For example, some have attempted to discern inflammation in the brain using diffusion tensor imaging (DTI) MRI. DTI MRI is successfully used with regularity to assess structures in the brain, such as white matter fibers. However, when attempting to assess neuro-inflammation using DTI, the lack of specificity inhibits clinical utility. Others have attempted to use positron emission tomography (PET) to image translocator protein (TSPO) due to its known role inflammatory response. However, such efforts struggle to provide quantitative information needed by clinicians. Further still, some have attempted to utilize microparticles of iron oxide (MPIO) to target neuro-inflammation and, thereby, image the inflammation with enhanced contrast using MRI. Unfortunately, such MPIO agents carry biocompatibility and/or toxicity concerns that limit utility. Thus, despite active research efforts to overcome these limitations, there remains no safe, widely accessible, and clinically viable neuroimaging methodology available for the in vivo study of neuro-inflammation.

Diffusion MRI can be used to measure tissue microstructure directly. One such approach is a model-based strategy in which a geometric model of the microstructure of interest predicts the MR signal from water diffusion within the tissue. A multi-compartment tensor models stands in contrast with DTI, which employs a single-compartment diffusion tensor model. As described herein, the multi-compartment model can be used to quantitatively express how the total normalized diffusion MRI signal is comprised by: (1) anisotropic diffusion within neuronal process and (2) anisotropic diffusion arising from around these processes. Some attempts to make multi-compartment diffusion models focused on the formulation and subsequent validation of mathematical models of water diffusion in neurites to garner estimates of neurite orientation as well as neurite density. Subsequent quantitative comparisons following co-registration of MR data with histology and light and electron microscopy demonstrated the relationship between the intracellular (intra-neurite) MR diffusion tensor and axonal/dendritic architecture.

Figure 1:
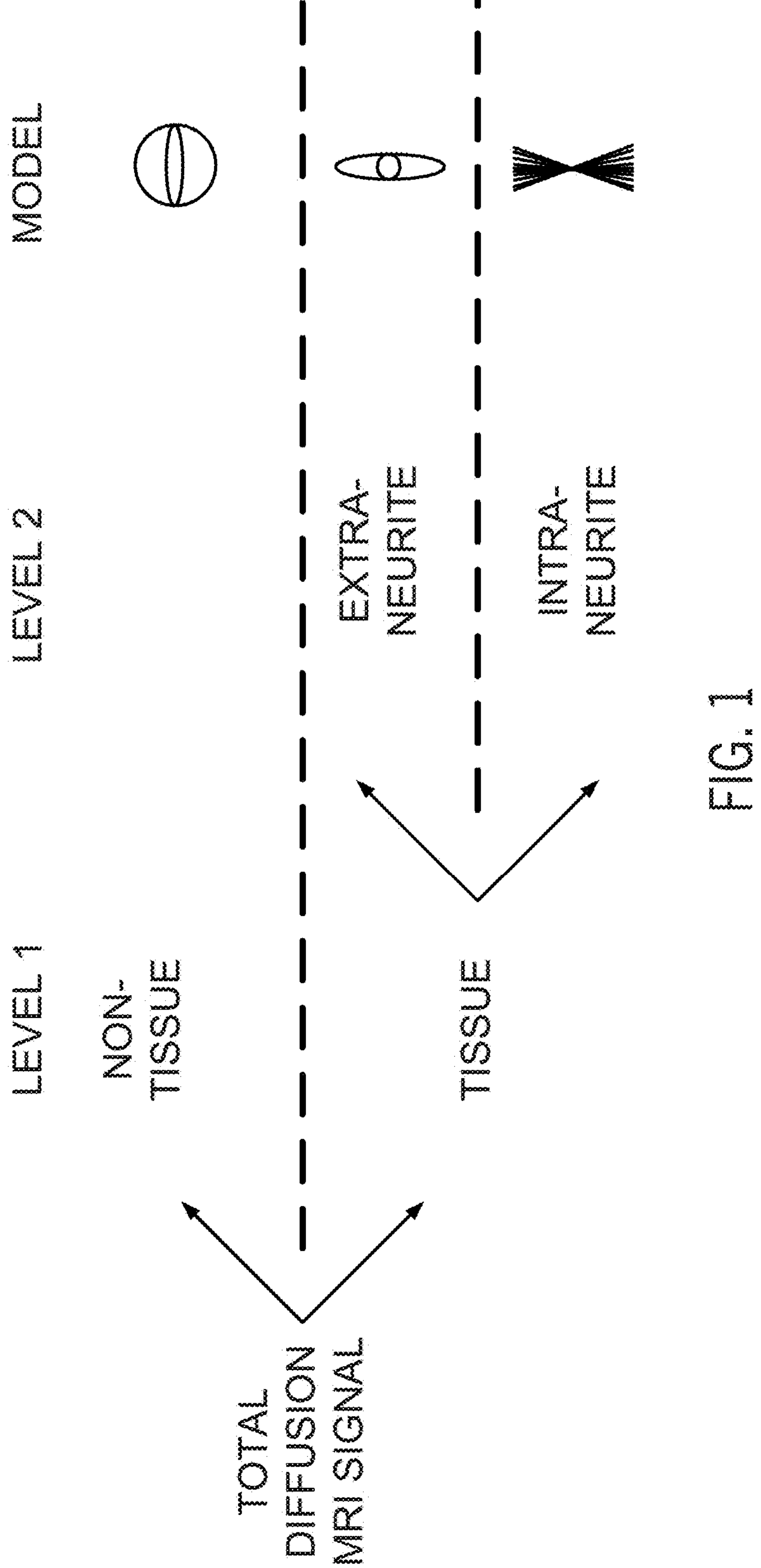
FIG. 1 is a graphic illustration of a tissue model in accordance with the present disclosure.

As illustrated in FIG. 1, the present disclosure provides a neurite orientation dispersion and density imaging (NODDI) model that advances multi-compartment diffusion imaging as a clinically feasible imaging technique. To generate greater tissue specificity than standard DWI techniques such as DTI, NODDI employs a model-based strategy designed to measure water diffusion arising from distinct tissue compartments. Specifically, FIG. 1 provides a NODDI tissue model in accordance with the present disclosure. The NODDI tissue model is a multi-compartmental model of the total normalized diffusion MRI signal and comprises: (1) non-tissue ($F_{iso}$); (2) extraneurite (orientation dispersion index, ODI); and (3) intraneurite (neurite density index, NDI). Non-tissue material, such as cerebral spinal fluid (CSF), represents a first level (level 1) of the model and can be modeled as a volume. Also at level 1 is tissue. However, unlike traditional models that models tissue as a single signal, the present disclosure includes a second level (level 2) that divides signal that otherwise would be attributed to "tissue" to be formed as extra-neurite material, such as cell bodies and glial cells (ODI) and intra-neurite material, such as axons and dendrites (NDI).

In the NODDI model, diffusivity in the extra-neurite compartment is measured by ODI, which was originally conceptualized to measure how changes in neurite dispersion influence water diffusivity in the extra-neurite space without accounting for the potential contribution that glial cells (such as microglia) can have on quantitative measures of ODI. However, within the extra-neurite compartment, glial cells reside, which account for a large percentage of non-neuronal cells. As microglia have been found to comprise 5-15% of all glial cells and, in response to inflammatory stimuli, undergo substantial changes in both morphology and density, these changes would be expected to significantly alter the degree of hindered diffusion in the extra-neurite compartment. These changes offer a potential opportunity to assess microglial activation and microglial mediated neuroinflammation by probing water diffusion using a modality such as MRI, but only if a model is utilized that enables the proper consideration of the underlying mechanisms.

The present disclosure recognizes that the NODDI model of FIG. 1 distinguishes three microstructural environments, including the intracellular, extracellular, and CSF compartments. The intracellular compartment (NDI) is defined by the space bounded by the membrane of neurites. The extracellular compartment (ODI) is defined by the space around the neurites, which includes neural cell bodies (somas) as well as glial cells.

Developed to be performed at clinical field strengths in 10-30 minutes, NODDI can interrogate individual tissue microstructural features. The present disclosure created a multi-compartment diffusion model that could be combined with NODDI to facilitate the assessment of neuro-inflammation. Though the multi-compartment model can be implemented in a variety of forms, in one non-limiting example, glia can be modeled to account for more than 35% of the non-neuronal cells and, more particularly, they can account for approximately 50% of the non-neuronal cells in the human brain. The extracellular compartment can be modeled as complimentary to the intracellular compartment, presuming that reductions in intracellular diffusion would be matched by a proportional reduction in extracellular diffusion, further discounting and excluding the contribution of glial cells to water diffusion within the extracellular space. With microglia comprising 5-15% of all glial cells and able to demonstrate up to a 35% change in absolute cell populations with an associated a 3-fold increase in total cell area, the present disclosure recognizes that microglia are an extraordinarily dynamic cell population of the CNS. Thus, contrary to prior assumptions, microglia can be modeled to significantly contribute to the diffusion tensor arising from the extracellular compartment. The present disclosure recognizes an association between microglial populations and parametric measures of NODDI with specific attention paid to understanding the relationship between ODI and microglial morphology and density. ODI is, thus, distinguished as an assessment of the extracellular compartment, from neurite density index (NDI), which is specific to the intracellular compartment. Thus, the present disclosure provides systems and methods including a multi-compartment diffusion model that can be used with NODDI to facilitate the assessment of neuro-inflammation through an assessment of ODI.

In particular, the present disclosure recognizes that neuroinflammation underlies numerous neurologic and neuropsychiatric disorders and noninvasive biomarkers to detect and monitor microglial inflammation are needed. The above-described multi-compartment diffusion tensor model applied to NODDI data allows for the direct biophysical interrogation of neurite density and orientation and also permits the simultaneous interrogation of the extracellular compartment and the neuropathological changes that can occur within this space, including changes related to microglia-mediated neuro-inflammation. Thus, the present disclosure allows the use of NODDI to measure changes in the extracellular compartment to noninvasively detect and measure microglial burden in the brain. This application can also be used to determine the quantitative relationship between microglial density with parametric measures of NODDI with quantitative immunofluorescence and stereology. The validation of NODDI to detect and monitor microglial neuroinflammation represents a major advance across a wide spectrum of neurologic and neuropsychiatric disorders with far reaching implications in clinical diagnosis, risk stratification, and therapeutic monitoring where a NODDI biomarker of neuro-inflammation can serve as a clinical endpoint assisting in the development of critically needed therapies. Further still, as NODDI can be performed on most clinically available MR scanners, there is a low barrier to the translation and dissemination of the results of this application into both the research and clinical setting so as to continue the development and refinement of NODDI for clinical care, clinical trials, and other clinical and research needs. Thus, the present disclosure provides a ready solution to a long-standing need that, despite having MRI hardware capable of implementing the present work, was not previously met or recognized.

To address the clinical gaps and unmet clinical needs described herein, the present disclosure provides an explanation across three major thematic areas: (1) conceptual, (2) biologically—relevant model system, and (3) quantitative analytic approach.

Conceptual.

The utility of multi-compartment diffusion tensor imaging techniques of NODDI extend beyond the determination of neurite architecture and orientation. Diffusion tensor data arising from the extracellular compartment captures neuropathological processes occurring in extra-neuronal space, including microglia-related changes associated with neuroinflammation. The high specificity of ODI can be used to track changes in microglial density across a broad range of experimental models with underlying microglial activation. This new conceptualization of NODDI and multi-compartment diffusion MR applied to the fields of neuroradiology and MR imaging meets needs in both.

Multi-compartment diffusion models biophysically model the total DWI signal as a sum of the diffusion weighted signal arising from a combination of biophysical compartments with different underlying cellular microstructures:

$$S = S_0 \sum_{i=0}^{n} w_i S_i; \quad \text{Eqn. 1}$$

where $S_0$ is the signal for the non-diffusion weighted (or b0) acquisitions, $w_i$ is the volume fraction, and $S_i$ is the signal function for the ith of n total compartments. In the NODDI model in accordance with the present disclosure, the diffusion MRI signal is described as a sum of three non-exchanging biophysical compartments:

$$S = (1 - v_{iso})(v_{ic} S_{ic} + (1 - v_{ic}) S_{ec}) + v_{iso} S_{iso}; \quad \text{Eqn. 2}$$

where S is the entire normalized signal; $S_{ic}$, $S_{ec}$, and $S_{iso}$ are the normalized signals of the intracellular, extracellular, and CSF compartments, respectively, and $v_{ic}$ and $v_{iso}$ are the normalized volume fractions of the intracellular and CSF compartments.

The systems and methods of the present disclosure can be applied to a variety of clinical applications. For non-limiting purposes of explanation, biologically-relevant model systems of acute and chronic microglial activation will be used. To capture the wide dynamic range in both the number of and morphological changes seen in microglia and how acute and chronic microglial activation can influence parametric measures of ODI, studies were performed to examine the performance of NODDI in the setting of acute microglial activation (following peripheral LPS administration) and chronic microglial activation in models of neuropsychiatric disease. Microglia display a tremendous range of morphologic variance and the degree of microglial ramification as well as the overall geometry of these microglial processes was anticipated to have an impact on the degree of hindered diffusion in the extracellular compartment. Towards this end, bidirectional changes were shown in parametric measures of ODI, which correspond to the various degrees of microglial ramification seen in the setting of acute and chronic microglial activation.

Quantitative Analytic Approach.

Studies were performed to determine the fundamental calibration of parametric measures of NODDI with microglial density. Following the elimination of microglia via CSF1R inhibition, serial NODDI was performed following inhibitor cessation as microglia repopulate the brain. Concurrent quantitative immunofluorescence and stereology was also performed to determine the relationship between microglial density and ODI at each time point. In addition to NODDI, standard diffusion tensor imaging was concomitantly performed to ascertain the performance of NODDI vis-à-vis DTI both in calibration experiments and acute and chronic microglial activation studies.

These methods allowed simultaneously analysis of the quantitative performance of NODDI and DTI in different settings of microglial activation and to also examine how our calibration measures perform in biologically-relevant experimental systems.

Figure 2:
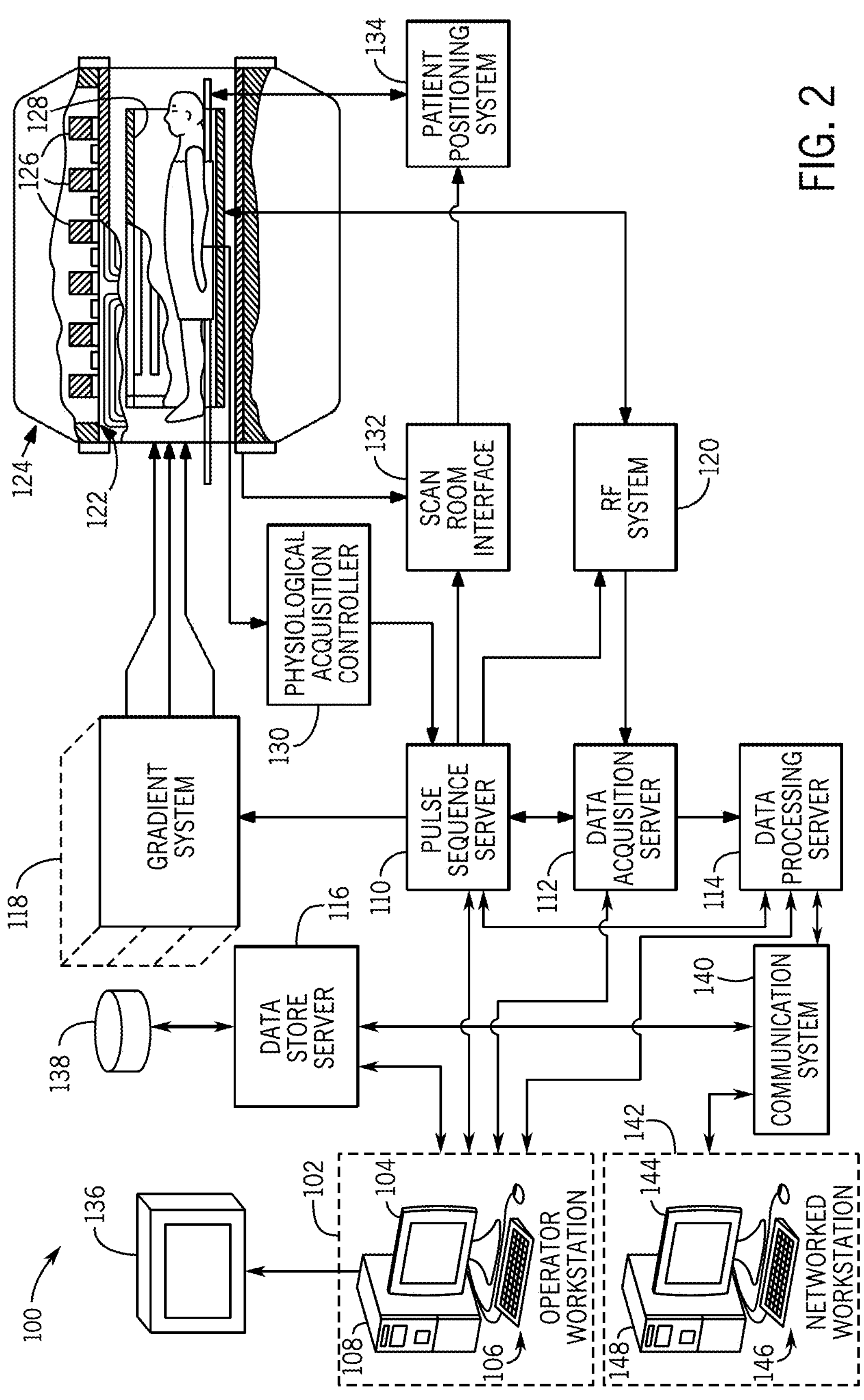
FIG. 2 is a block diagram of an exemplary magnetic resonance imaging ("MRI") system configured in accordance with the present disclosure.

Referring now to FIG. 2, a magnetic resonance imaging ("MRI") system 100 configured to carry out the processes and techniques described herein is illustrated in FIG. 2. The MRI system 100 includes an operator workstation 102, which will typically include a display 104, one or more input devices 106 (such as a keyboard and mouse or the like), and a processor 108. The processor 108 may include a commercially available programmable machine running a commercially available operating system. The operator workstation 102 provides the operator interface that enables scan prescriptions to be entered into the MRI system 100. In general, the operator workstation 102 may be coupled to multiple servers, including a pulse sequence server 110; a data acquisition server 112; a data processing server 114; and a data store server 116. The operator workstation 102 and each server 110, 112, 114, and 116 are connected to communicate with each other. For example, the servers 110, 112, 114, and 116 may be connected via a communication system 140, which may include any suitable network connection, whether wired, wireless, or a combination of both. As an example, the communication system 140 may include both proprietary or dedicated networks, as well as open networks, such as the internet.

The pulse sequence server 110 functions in response to instructions downloaded from the operator workstation 102 to operate a gradient system 118 and a radiofrequency ("RF") system 120. Gradient waveforms to perform the prescribed scan are produced and applied to the gradient system 118, which excites gradient coils in an assembly 122 to produce the magnetic field gradients $G_x$, $G_y$, $G_z$ used for position encoding magnetic resonance signals. The gradient coil assembly 122 forms part of a magnet assembly 124 that includes a polarizing magnet 126 and a whole-body RF coil 128.

RF waveforms are applied by the RF system 120 to the RF coil 128, or a separate local coil (not shown in FIG. 2), in order to perform the prescribed magnetic resonance pulse sequence. Responsive magnetic resonance signals detected by the RF coil 128, or a separate local coil, are received by the RF system 120, where they are amplified, demodulated, filtered, and digitized under direction of commands produced by the pulse sequence server 110. The RF system 120 includes an RF transmitter for producing a wide variety of RF pulses used in MRI pulse sequences. The RF transmitter is responsive to the scan prescription and direction from the pulse sequence server 110 to produce RF pulses of the desired frequency, phase, and pulse amplitude waveform. The generated RF pulses may be applied to the whole-body RF coil 128 or to one or more local coils or coil arrays.

The RF system 120 also includes one or more RF receiver channels. Each RF receiver channel includes an RF preamplifier that amplifies the magnetic resonance signal received by the coil 128 to which it is connected, and a detector that detects and digitizes the I and Q quadrature components of the received magnetic resonance signal. The magnitude of the received magnetic resonance signal may, therefore, be determined at any sampled point by the square root of the sum of the squares of the I and Q components:

$$M = \sqrt{I^2 + Q^2}; \quad \text{Eqn. 3}$$

and the phase of the received magnetic resonance signal may also be determined according to the following relationship:

$$\varphi = \tan^{-1}\left(\frac{Q}{I}\right). \quad \text{Eqn. 4}$$

The pulse sequence server 110 also optionally receives patient data from a physiological acquisition controller 130. By way of example, the physiological acquisition controller 130 may receive signals from a number of different sensors connected to the patient, such as electrocardiograms from electrodes, or respiratory signals from a respiratory bellows or other respiratory monitoring device. Such signals are typically used by the pulse sequence server 110 to synchronize, or "gate," the performance of the scan with the subject's heart beat or respiration.

The pulse sequence server 110 also connects to a scan room interface circuit 132 that receives signals from various sensors associated with the condition of the patient and the magnet system. It is also through the scan room interface circuit 132 that a patient positioning system 134 receives commands to move the patient to desired positions during the scan.

The digitized magnetic resonance signal samples produced by the RF system 120 are received by the data acquisition server 112. The data acquisition server 112 operates in response to instructions downloaded from the operator workstation 102 to receive the real-time magnetic resonance data and provide buffer storage, such that no data is lost by data overrun. In some scans, the data acquisition server 112 does little more than pass the acquired magnetic resonance data to the data processor server 114. However, in scans that require information derived from acquired magnetic resonance data to control the further performance of the scan, the data acquisition server 112 is programmed to produce such information and convey it to the pulse sequence server 110. For example, during prescans, magnetic resonance data is acquired and used to calibrate the pulse sequence performed by the pulse sequence server 110. As another example, navigator signals may be acquired and used to adjust the operating parameters of the RF system 120 or the gradient system 118, or to control the view order in which k-space is sampled. In still another example, the data acquisition server 112 may also be employed to process magnetic resonance signals used to detect the arrival of a contrast agent in a magnetic resonance angiography ("MRA") scan. By way of example, the data acquisition server 112 acquires magnetic resonance data and processes it in real-time to produce information that is used to control the scan.

The data processing server 114 receives magnetic resonance data from the data acquisition server 112 and processes it in accordance with instructions downloaded from the operator workstation 102. Such processing may, for example, include one or more of the following: reconstructing two-dimensional or three-dimensional images by performing a Fourier transformation of raw k-space data; performing other image reconstruction techniques, such as iterative or backprojection reconstruction techniques; applying filters to raw k-space data or to reconstructed images; generating functional magnetic resonance images; calculating motion or flow images; and so on.

Images reconstructed by the data processing server 114 are conveyed back to the operator workstation 102. Images may be output to operator display 112 or a display 136 that is located near the magnet assembly 124 for use by attending clinician. Batch mode images or selected real time images are stored in a host database on disc storage 138. When such images have been reconstructed and transferred to storage, the data processing server 114 notifies the data store server 116 on the operator workstation 102. The operator workstation 102 may be used by an operator to archive the images, produce films, or send the images via a network to other facilities.

The MRI system 100 may also include one or more networked workstations 142. By way of example, a networked workstation 142 may include a display 144, one or more input devices 146 (such as a keyboard and mouse or the like), and a processor 148. The networked workstation 142 may be located within the same facility as the operator workstation 102, or in a different facility, such as a different healthcare institution or clinic. The networked workstation 142 may include a mobile device, including phones or tablets.

The networked workstation 142, whether within the same facility or in a different facility as the operator workstation 102, may gain remote access to the data processing server 114 or data store server 116 via the communication system 140. Accordingly, multiple networked workstations 142 may have access to the data processing server 114 and the data store server 116. In this manner, magnetic resonance data, reconstructed images, or other data may exchanged between the data processing server 114 or the data store server 116 and the networked workstations 142, such that the data or images may be remotely processed by a networked workstation 142. This data may be exchanged in any suitable format, such as in accordance with the transmission control protocol ("TCP"), the internet protocol ("IP"), or other known or suitable protocols.

Figure 3:
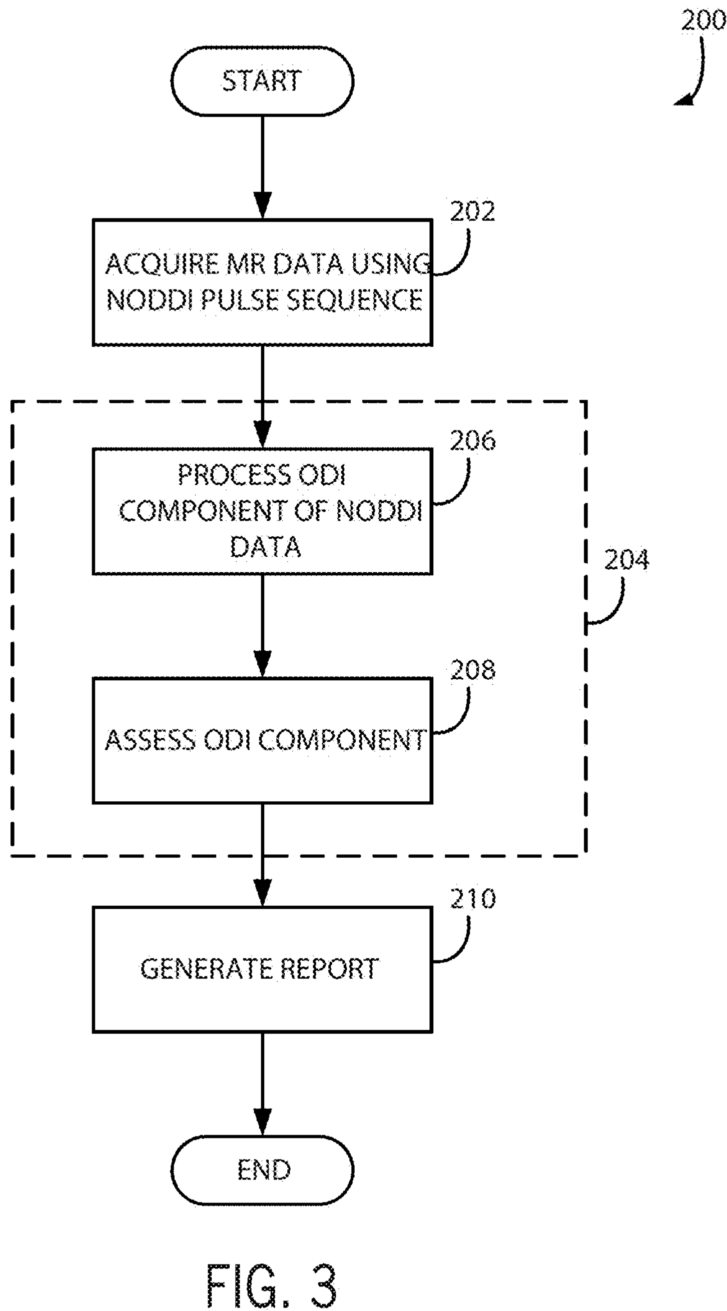
FIG. 3 is a flow chart setting forth steps of a process utilizing the model and system of FIGS. 1 and 2 in accordance with the present disclosure.

The system of FIG. 2 can be used to perform a process for assessing neuro-inflammation in accordance with the present disclosure. Specifically, referring to FIG. 3, a process 200 in accordance with the present disclosure begins at process block 202 by acquiring MR data using a NODDI pulse sequence. The general process for acquiring NODDI MR data is described in Zhang, H., Schneider, T., Wheeler-Kingshott, C. A., and Alexander, D. C., NODDI: practical in vivo neurite orientation dispersion and density imaging of the human brain. Neuroimage 61, 1000-1016 (2012), which is incorporated herein by reference in its entirety. That is, as generally indicated at sub-process 204, the acquired NODDI data is process to assess parametric measures of NODDI. More particularly, the NODDI data is processed to assess changes in microglial density and morphology that are associated with neuro-inflammation. This assessment is predicated upon an understanding of the present disclosure related to the (i) fundamental relationship between microglial populations and measures of NODDI and (ii) sensitivity to changes in microglial morphology and their populations in model systems of acute and chronic microglial activation.

At process block 206, the NODDI data is processed to derive the orientation dispersion index (ODI) component of the NODDI data. The present disclosure recognizes that alterations in microglia morphology in a model of acute inflammation increases anisotropic diffusion in the extracellular compartment and yields an increase in the ODI component of the NODDI imaging data. That is, the present disclosure recognizes the unique sensitivity and specificity of ODI to alterations in microglial morphology occurring in the extracellular compartment during acute microglial activation.

At process block 208, the ODI component is assessed. This may be performed in any of a variety of ways. For example, the ODI component may be assessed based on the current set of NODDI data to determine acute neuro-inflammation. Additionally or alternatively, the ODI component of the NODDI data may be assessed against longitudinal or other temporal information to track changes in the extracellular compartment following peripheral inflammation, or to determine whether any acute neuro-inflammation is part of a greater chronic inflammation and, if so, the directionality of the chronic inflammation. That is, in a longitudinal study, the assessment of the ODI component at process block 208 may include directional measures of indicators of inflammation.

As one non-limiting example, an increase in ODI generally indicates a potential for continued increase in ODI (in both tract-based spatial statistics (TBSS) and within a given region of interest (ROI)). As such, longitude assessments over multiple imaging sessions can be performed to assess whether inflammation indicated by a given ODI increase does continue, or recedes.

That is, the present disclosure recognizes that an overall decrease in ODI is consistent a decreased microglia density and altered microglia morphology. In contradistinction to the morphologic changes occurring in microglia during acute activation, chronically activated microglia exhibit fewer ramified processes, decreased surface area, and shorter, fewer, and thicker processes emanating from the cell body. These morphometric changes facilitate water diffusion in the extracellular compartment, which manifest as a decrease in ODI. Furthermore, salient regions of the brain include the basal ganglia, neocortex, and corpus callosum (genu, body, splenium).

Thus, at process block 210 a report can be generated that provides clinically-focused information. For example, as described above, acute and longitudinal and/or chronic inflammation information can be provided in text or images or a combination thereof. Furthermore, the report may include particular clinical indicators relative to particular conditions. For example, morphological changes in microglia among different brain regions in the presence of schizophrenia can be assessed using ODI analysis. In particular, an overall decrease in ODI is consistent with chronic microglial activation in schizophrenia. As another example, changes in microglial density among different brain regions following CSF1R inhibition can be assessed using ODI. In particular, as microglia decrease, there is a decrease in the degree of hindered diffusion in the extracellular compartment as modeled by NODDI, which can be seen through a decrease in ODI.

Therefore, the ODI component of NODDI data can be used as a quantitative neuroimaging or neuro-inflammation measure that is sufficiently sensitive to detect and monitor microglial density throughout the brain and be correlated to particular clinical diagnosis or pathologies as an assessment of the extracellular compartment.

EXAMPLES

To test how cellular changes in the extra-neurite space (microglial density) impacts the measured diffusion signal from the extra-neurite space (ODI, orientation dispersion index), an in silico diffusion experiment using multiple Monte Carlo random walk simulations, as implemented in Camino, was performed by varying the number of modeled cells in the extra-neurite space. To generate the components of the multi-compartment diffusion model, basic geometrical components representing white matter axons and microglia were constructed in Blender (Blender Foundation, Amsterdam, Netherlands). We constructed a series of 6 undulating cylinders (with no dispersion) modeling axons in a similar manner as previously described by Kamiya et al., 2017 with radius=1 μm, length=40 μm, undulation amplitude A=2, to yield a final $\lambda$=1.024 to simulate a voxel in a white matter tract. Icospheres were next modeled as simplified microglia in the extra-neurite space and were generated with a radius=5 μm. The cylinders were then hexagonally packed without touching within the simulated volume (40×40×40 μm) with all components placed within the model in MatLab (version 2015a, MathWorks, Natick, MA, USA). 10 simulations of 0, 5, 15, and 25 spheres were performed with spheres randomly distributed throughout the extra-neurite space of the modeled volume. The volume fraction of the bundled axons is 2.7%; the volume fraction of the spheres is 6.3%, 18.9%, and 31.5% for 5, 15, and 25 spheres, respectively. Each simulation comprised of 100,000 spins and 5,000 time steps. The free diffusivity was set at $0.6\times10^{-9}$ $m^2/s$ per recommendations in Camino. From the simulated random walks of particles, a virtual MRI signal was obtained using the NODDI acquisition scheme used in our ex-vivo samples with the addition of Gaussian noise to the simulated signal with SNR=50 of the b=0 signal for each run. The mean ODI was calculated for each simulation. Diffusion tensor indices of fractional anisotropy (FA) and mean diffusivity (MD) were also calculated.

Animals and Reagents

All experiments were performed in accordance with animal protocols approved by the Institutional Animal Care and Use Committee at our institution (Protocol #: M005899). 12-week-old C57BL/6J male mice (Charles River Laboratories, MA, USA) were used for all experiments and were randomly assigned to control or experimental CSF1R inhibition cohorts. Control animals were maintained on AlN-76A standard chow (Research Diets, NJ, USA); animals receiving CSF1R inhibition received AlN-76A admixed with the CSF1R inhibitor PLX5622 (Plexxikon, CA, USA; 1,200 mg/kg) as previously described (Elmore et al., 2014). Animals receiving CSF1R inhibition were maintained on their admixed diet for 8-days; on day 8, CSF1R inhibition was withdrawn by replacing their chow with standard chow (AlN-76A). For each time point, mice from the control and the experimental groups were sacrificed on days 0, 9, 11, and 15 (n=48; n=6, each time point; control and experimental).

MRI Acquisition

Data Acquisition: On days 0, 9, 11, and 15, mice were brought to a surgical plane of anesthesia with isoflurane then transcardially perfused with phosphate-buffered solution (PBS) followed by 4% paraformaldehyde (PFA) in 0.1 M PBS. Brains were extracted from the cranial vault and post-fixed in PFA. Imaged brains were placed in a custom-built holder immersed in Fluorinert (FC-3283, 3 M, St. Paul, MN, USA) and imaged with a 4.7-T Agilent MRI system with a 3.5-cm diameter quadrature volume RF coil. Multi-slice, diffusion-weighted, spin echo images were used to acquire 10 non-diffusion weighted images (b=0 s·mm$^{-2}$) and 75 diffusion-weighted images (25: b=800 s·mm$^{-2}$, 50: b=2,000 s·mm$^{-2}$), using non-colinear diffusion-weighting directions. Other imaging parameters: TE/TR=24.17/2000-ms, FOV=30×30 mm$^2$, matrix=192×192 reconstructed to 256×256 for an isotropic voxel size of 0.25-mm over two signal averages. All animals were used in subsequent analyses.

Data Preprocessing and Region of Interest (ROI) Analysis: Raw data files were converted to NIfTI format and FSL was used to correct for eddy current artifacts with Eddy-correct. FSL output volumes were converted to NIfTI tensor format for use with the DTI-TK software package. DTI-TK (Zhang et al., 2006) was used to estimate a study-specific tensor template, to which subject tensor volumes were spatially normalized. The NODDI model was then voxel-wise fitted to the diffusion data in Matlab (The MathWorks, Inc., Natick, MA) with the NODDI toolbox (available at from nitrc.org). An additional compartment of isotropic restriction was employed for ex-vivo studies. A manual ROI was drawn over the left dentate gyrus from anatomically defined areas on a normalized mean diffusion map. The ROI was overlaid over subjects from each of the two groups (±CSF1R treatment) and ODI, FA, and MD were calculated.

Immunofluorescent Staining and Quantification

Following imaging, brains were removed from their custom holders and were returned to ice-cold 4% PFA for 24 h, then in a 30% sucrose solution (Alfa Aesar, Ward Hill, MA; Cat #36508) in 0.1 M PBS (Growcells, Irvine, CA; Cat #MRGF-6235). Frozen coronal sections were taken at 40 μm using a cryostat (Leica CM 1850, Wetzlar, Germany) and stored short-term in PBS at 4° C. until staining. Floating sections were incubated in blocking solution formulated with 0.1 M PBS, 2% bovine serum albumin (Fisher Scientific, Hampton, NH; Cat #BP9706-100) and 0.1% sodium azide (Sigma, St. Louis, MO; Cat #S2002) for 1 h at room temperature (RT), then incubated overnight at 4° C. with primary antibodies for Iba-1 (rabbit Anti-Iba-1, dilution 1:2000, Abcam, Cambridge, MA, Cat #AB178847), NeuN (chicken Anti-NeuN, dilution 1:1500; EMD Millipore, Billerica, MA Cat #ABN91MI), and GFAP (mouse Anti-GFAP, dilution 1:1000; Thermo Fisher Scientific, Waltham, MA Cat #PIMA512023). Sections were incubated for 1 h at RT with the corresponding Alexa 488-, 555-, 647-labeled species specific secondary antibodies (goat anti-rabbit, Abcam, Cambridge, MA, Cat #AB150077; goat anti-chicken, Thermo Fisher Scientific, Waltham, MAformer Invitrogen Cat #A-21437; goat anti-mouse, Abcam, Cambridge, MA, Cat #AB150115; all diluted at 1:2000). Sections were counterstained with 0.1 μm/mL 4',6-diamidino-2-phenylindole (DAPI) (Novus Biologicals, Littleton, CO; Cat #NBP2-31156) for 5 min at RT, then mounted with Fluoromount-G (Southern Biotech, Birmingham, AL, Cat #0100-01). Images of the left hippocampus were acquired with a Leica DMi8 Inverted Fluorescent microscope (Wetzlar, Germany) with a 10× dry objective lens. All microscopy images were analyzed using ImageJ. The Region of Interest (ROI) manager tool was used to isolate the hippocampus. Images were made binary via manual thresholding, then the Particle Analyzer tool was used to automatically count cells.

Statistical Analysis

Imaging sample sizes and power analyses are based on standard deviations from previous studies with a significance level of 5% and power of 90%. Statistical tests were performed in GraphPad Prism or R. Analysis of cell counts between control and CSF1R-inhibitor diet were performed using a two-tailed unpaired Student's t-test; $p<0.05$ was established as the significance level. Kendall's tau coefficient was calculated to measure the non-parametric, ordinal association between microglial cell counts and mean ODI from three time-points in CSF1R administered animals.

Results

Computational Modeling of the Extra-Neurite Space in Multi-Compartment MRI

Figure 4:
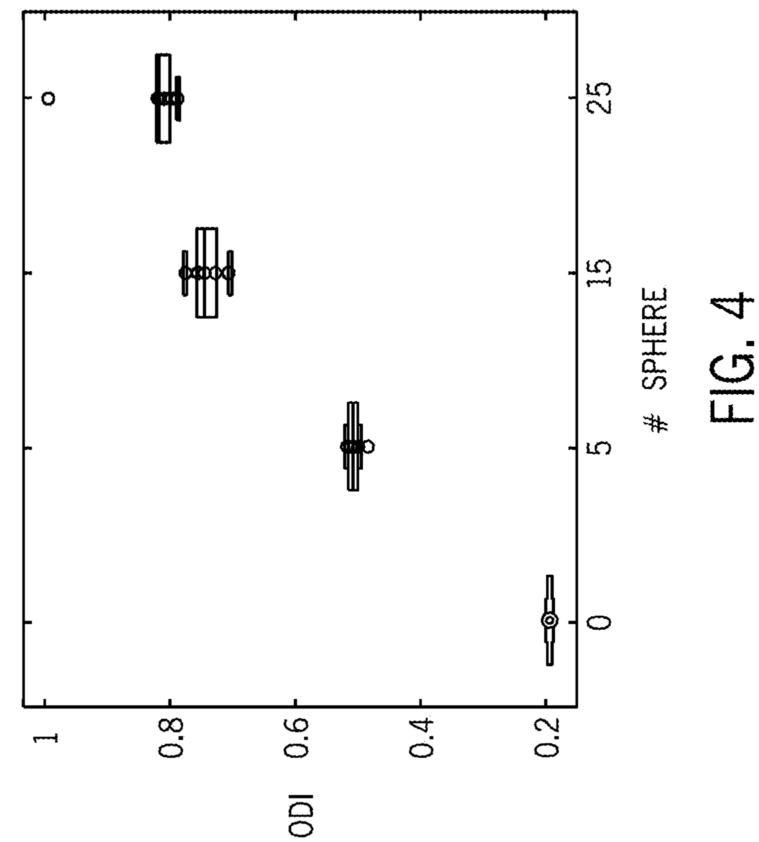
FIG. 4 shows a box plot of pulsed gradient water diffusion simulations within a representative voxel.

As the NODDI model includes parameters to measure water diffusion in the extra-neurite space, we hypothesized that changes in microglial density would change the water diffusivity measured within the extra-neurite compartment. To test this hypothesis and to first ascertain the sensitivity of the extra-neurite compartment to the cellular changes of neuroinflammation, we performed an in silico diffusion experiment utilizing a Monte Carlo random walk simulation with NODDI acquisition parameters, the results of which are shown in FIG. 4. FIG. 4 shows a box plot of pulsed gradient water diffusion simulations within a representative voxel that were performed with 0, 5, 15, and 25 spheres present (representing extra-neurite cellular elements) demonstrating increased ODI as a function of increased occupancy of the extra-neurite space. Within a simulated voxel with a modeled undulating axon bundle (to replicate a white matter tract), we varied the number of modeled microglia within the simulated voxel over multiple iterative simulations to assess the sensitivity of NODDI to these microglial changes in the extra-neurite space expected during neuroinflammation. FA and MD were also calculated. As shown in FIG. 4, an increase in the number of microglia accompanies a concomitant increase in ODI, demonstrating that increased occupancy within the extra-neurite space is coupled with increased hindered water diffusion. Our simulation of a voxel in a white matter tract also importantly finds that measures of ODI are independent of neurite dispersion, for which ODI was originally modeled to measure. In Monte Carlo simulations with only the axon bundle present (no microglia), our simulations return a non-zero value of ODI, supporting the hypothesis that any structure localizing to the extra-neurite space (such as the modeled axon bundle) is able to contribute to alterations in water diffusivity within the extra-neurite compartment and thus to calculated values of ODI.

Figure 5:
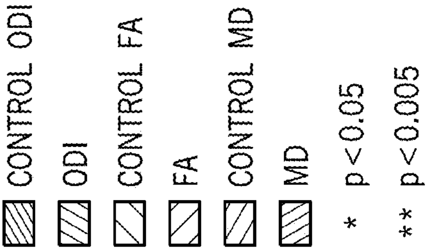
FIG. 5 shows a graph of orientation dispersion index (ODI), fractional anisotropy (FA), and mean diffusivity (MD) index levels of a control group and a CSF1R inhibited group of mice at day 1, day 3, and day 7 following inhibitor withdrawal in the inhibited group.
Figure 5:
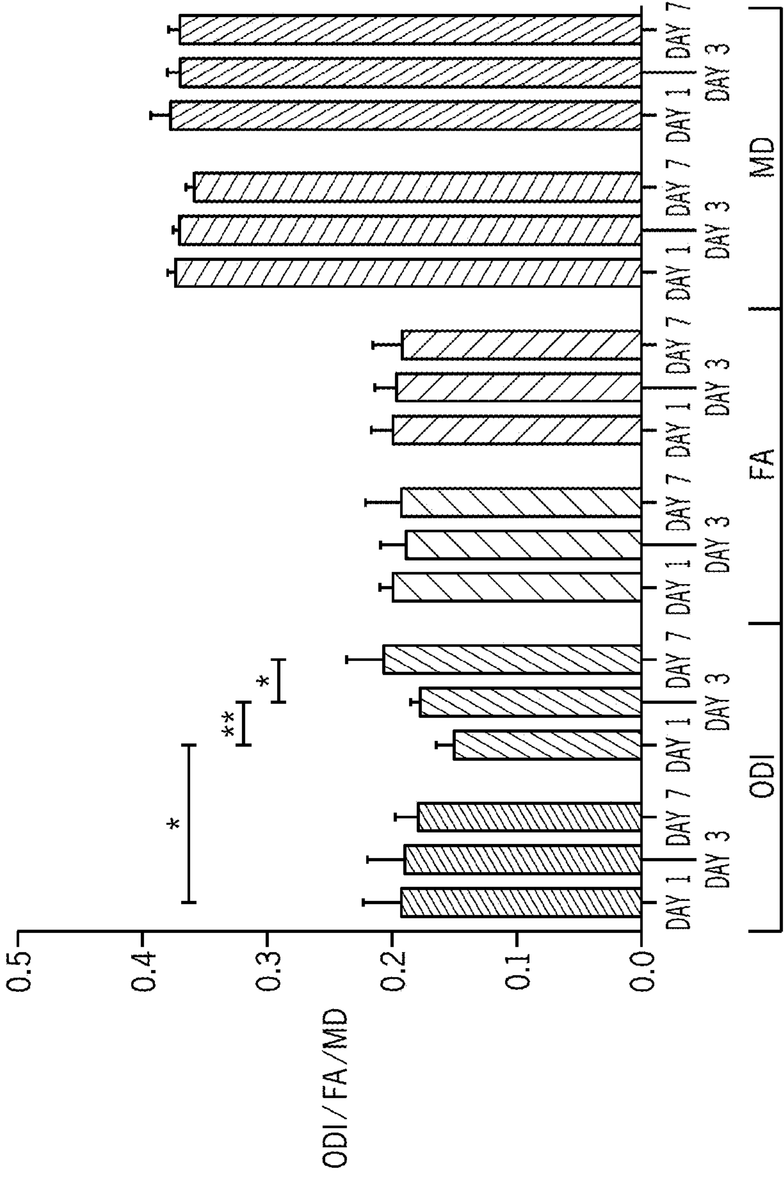

Quantitative Diffusion MRI of the Extra-Neurite Space is Sensitive to Microglial Density The extra-neurite compartment includes microglia and other cell populations including astrocytes, oligodendrocytes, ependymal cells, and vascular structures, all of which could be expected to impact the degree of hindered diffusion in the extra-neurite space. To examine the contribution of microglia to the measured diffusion tensor arising from the extra-neurite compartment in the NODDI model, we selectively eliminated microglia from the brain via CSF1R inhibition to specifically characterize the relationship between quantitative measures of ODI and microglial density. Following the complete elimination of microglia from the brain following CSF1R inhibition, CSF1R inhibition was withdrawn and NODDI imaging of the dentate gyrus of the hippocampus was performed 1, 3, and 7 days after inhibitor withdrawal. As shown in FIG. 5, at day 1 post-withdrawal during which few microglia are present, we find a statistically significant decrease in ODI when compared to control animals (no CSF1R inhibition) consistent with results derived from our in silico model. As microglia begin to repopulate the brain following the cessation of CSF1R inhibition, there is an increase in ODI on days 3 and 7, consistent with our in silico model's prediction, and further supports both the role of microglia and their contribution to water diffusivity in the extra-neurite space as well as the overall sensitivity of NODDI to capture the cellular changes in microglial density throughout the extra-neurite space. No statistically significant changes in FA or MD were found.

Microglial Density is Strongly Correlated with ODI

Figure 6:
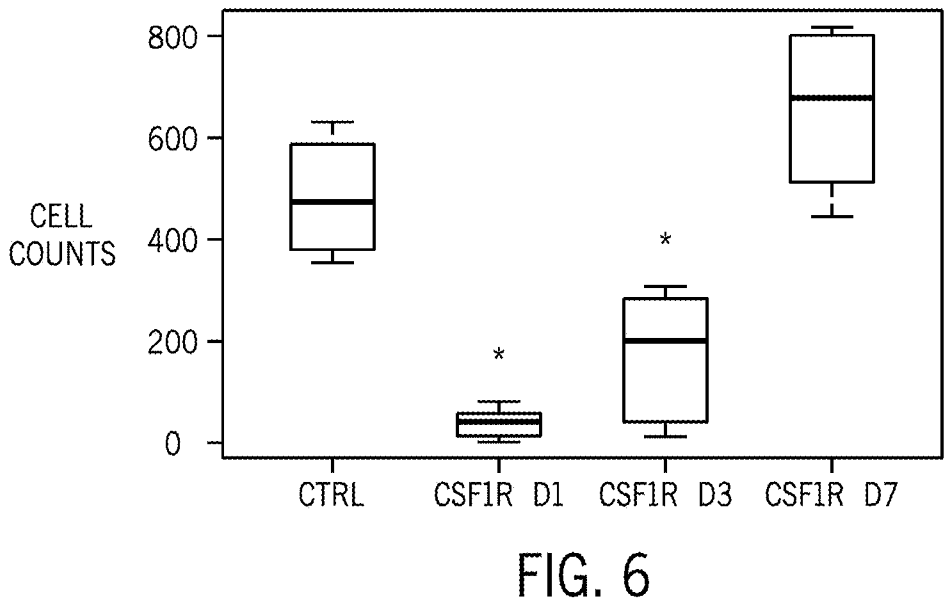
FIG. 6 shows a box plot of microglia cell counts of a control group and a CSF1R inhibited group of mice at day 1, day, and day 7 following CSF1R inhibitor withdrawal.
Figure 7:
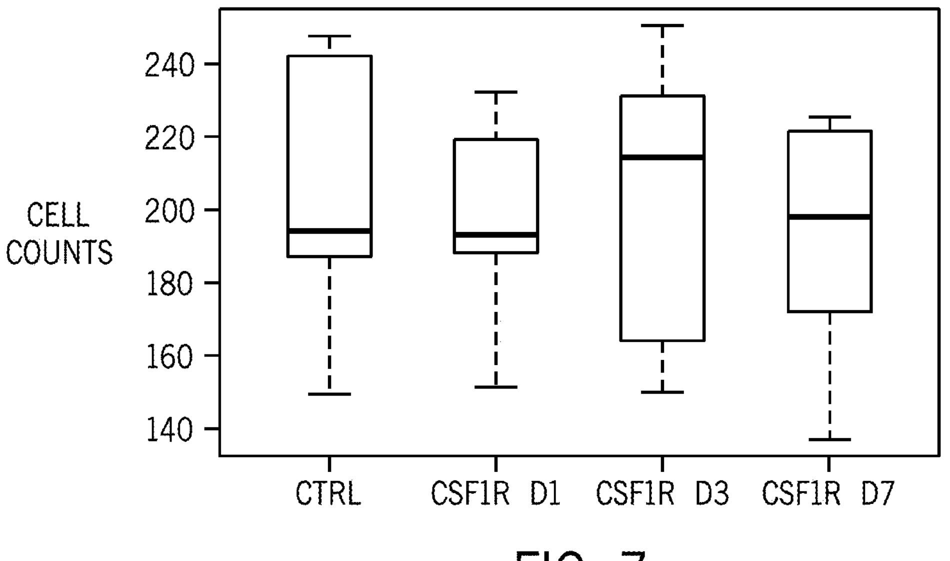
FIG. 7 shows a box plot of neuron cell counts of a control group and a CSF1R inhibited group of mice at day 1, day, and day 7 following CSF1R inhibitor withdrawal.
Figure 8:
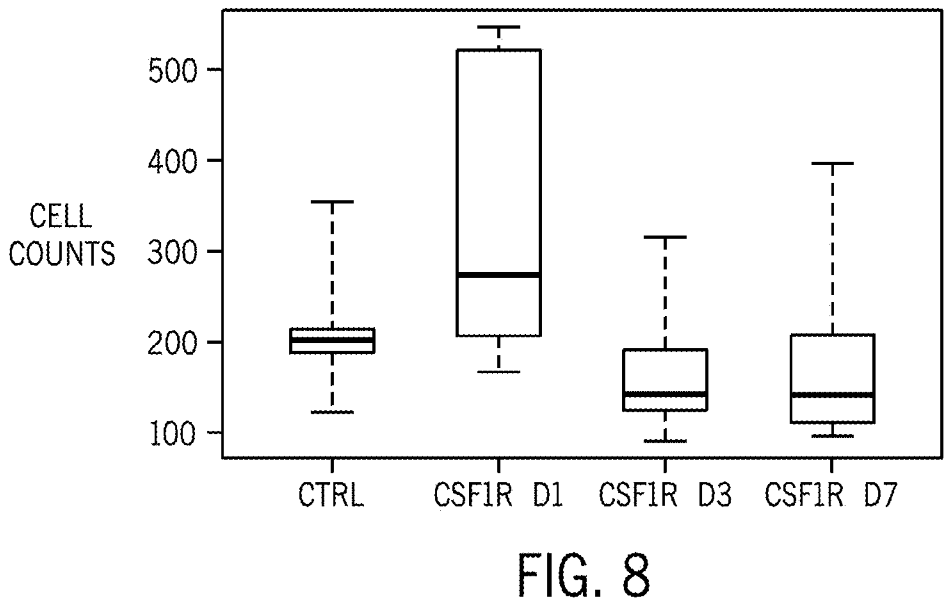
FIG. 8 shows a box plot of astrocytes cell counts of a control group and a CSF1R inhibited group of mice at day 1, day, and day 7 following CSF1R inhibitor withdrawal.
Figure 9:
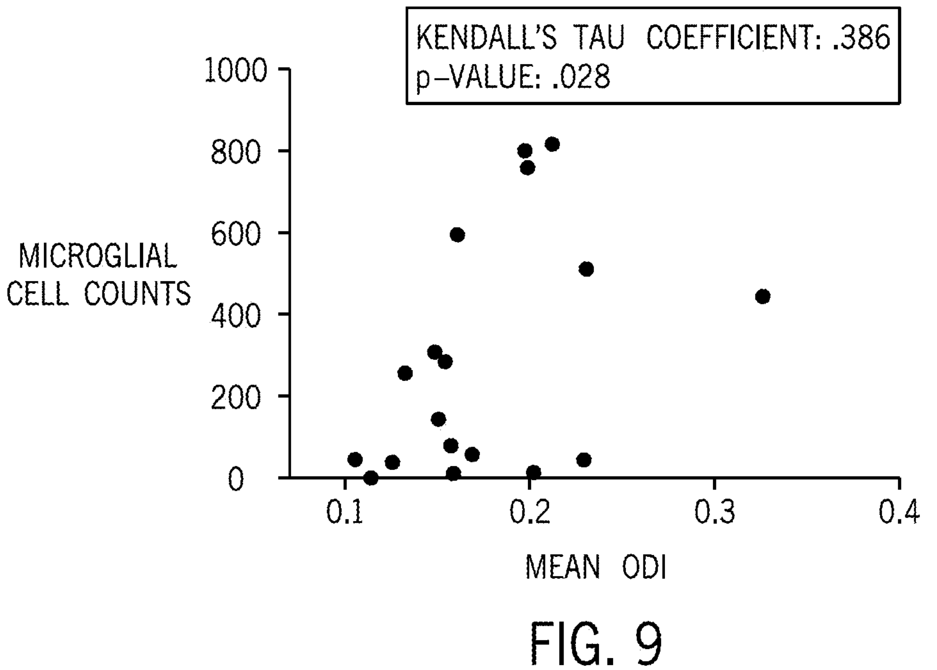
FIG. 9 shows a graph of microglial cell counts plotted against mean ODI 1, 3, and 7 days post CSF1R inhibition in mice.

To further establish whether the measured increase in mean ODI correlates with changes in microglial density, sections of the imaged brains at 1, 3, and 7 days following CSF1R inhibition were stained with Iba1, NeuN, and GFAP to identify microglia, neurons, and astrocytes, respectively. Stained and quantified sections were taken at the level of the hippocampal head that were to co-registered to mean FA maps. Immunofluorescent (IF) staining showed successful microglial depletion following 8 days of CSF1R inhibition with further IF quantification demonstrating no significant difference in neurons or astrocytes (data not shown), recapitulating data previously shown by Elmore et al. (2014). As shown in FIGS. 6-8, at 1, 3, and 7 days following withdrawal of CSF1R inhibition, there is a steady repopulation of microglia throughout the dentate gyrus, again with no significant change in other major cells populations present in the extra-neurite space. Specifically, as shown by FIG. 6, microglia are depleted with CSF1R inhibition and begin to repopulate the brain following CSF1R inhibitor withdrawal. On days 1 and 3 post-withdrawal, microglial counts are still significantly reduced compared to control (*$p<0.05$). FIGS. 7 and 8 show cell counts of neurons and astrocytes respectively. Both neurons and astrocytes demonstrated no significant change in density throughout CSF1R inhibitor treatment or withdrawal. With ODI values and quantitative IF data for the number of microglia present, a Kendall's tau coefficient was calculated to measure the non-parametric, ordinal association between microglial cell counts and mean ODI from these three time points in CS1R administered animals. As shown in FIG. 9, with a Kendall's tau of 0.386 ($p=0.028$), we demonstrate that there is a significant association between measured values of ODI and microglial density, and that ODI is positively correlated to microglial density. Kendall's tau demonstrates a significant association between measured microglial cell counts and mean orientation dispersion index 1, 3, and 7 days post CSF1R inhibition demonstrating that microglial density is positively correlated with quantitative measures of anisotropic diffusion arising from the extra-neurite space. These results also align with our in silico analysis and show that microglial density is positively correlated with quantitative measures of greater hindered diffusion arising from the extra-neurite space.

In this disclosure, we first demonstrated the sensitivity of the NODDI model to capture changes in microglial density, whereby increased occupancy of the extra-neurite space is correlated with greater hindered diffusion. We also showed that NODDI is sensitive to microglial density following microglial depletion with CSF1R inhibition and subsequent repopulation after drug removal, revealing that microglial density is a key contributor to quantitative measures of hindered diffusion in the extra-neurite space. Finally, we demonstrate the significant statistical correlation between microglial density with quantitative measures of ODI, showing that microglial density is positively correlated with hindered diffusion in the extra-neurite space. Together these data provide the first example of MRI to track the cellular changes associated with microglial activation during neuroinflammation.

The ability to track microglial activation via changes in microglial density throughout stages of neuroinflammation illustrates that the systems and methods of the present disclosure provide major advance in clinical care and research across a large spectrum of neurologic and psychiatric disease, particularly in clinical diagnostic accuracy, patient risk stratification, and therapeutic monitoring of neuroinflammation.

As a parallel to tracking disease progression, NODDI may also provide a useful neuroimaging biomarker for evaluating the efficacy of new therapeutics. In diseases like Alzheimer's disease (AD), where neuroinflammation is recognized as a key driving force of disease progression, therapeutic research is shifting toward targets that may help control the inflammatory response. Clinical evaluation of AD is difficult and relies heavily on observation of symptoms. Although PET has been proposed as a potential method of monitoring AD progression as well as responsivity to anti-inflammatory therapies, PET methods such as TSPO (translocator protein) imaging harbor a number of limitations including genotypic variation, complex tracer kinetics, and variability of plasma free fractions across human clinical cohorts.

In summary, the above results demonstrate that NODDI parameters corresponding to the extra-neurite compartment can sensitively detect a broad range of microglial densities in the extraneurite compartment. With microglial density serving as an important biomarker of disease activity and chronicity across a broad-spectrum of neurologic and psychiatric disease, our results highlight the potential for NODDI and other multicompartment diffusion MRI techniques to detect the cellular changes of microglial-mediated neuroinflammation toward improving clinical diagnostic accuracy, patient risk stratification, and therapeutic monitoring.

The above-described system may be configured or otherwise used to carry out processes in accordance with the present disclosure. In particular, as will be described in further detail, The present invention has been described in terms of one or more preferred embodiments, and it should be appreciated that many equivalents, alternatives, variations, and modifications, aside from those expressly stated, are possible and within the scope of the invention.

The invention claimed is:

1. A method for non-invasively assessing neuro-inflammation in a subject comprising:

acquiring, using a computer system, neurite orientation dispersion and density imaging (NODDI) data of the subject;

processing, using the computer system, the NODDI data to determine an orientation dispersion index (ODI) component of the NODDI data;

assessing, using the computer system, the ODI component against one of a reference of neuro-inflammation or a prior ODI component acquired from the subject to distinguish an acute neuro-inflammation in the subject from chronic neuro-inflammation in the subject and quantify the acute neuro-inflammation or the chronic neuro-inflammation; and generating, using the computer system, a report indicating the quantified acute neuro-inflammation or the quantified chronic neuro-inflammation in the subject.

2. The method of claim 1 wherein the reference of neuro-inflammation relates changes in ODI to changes in extracellular compartments in brain tissue.

3. The method of claim 2 wherein the changes in extracellular compartments include microglial cell density and morphology that are associated with neuro-inflammation.

4. The method of claim 1 wherein assessing the ODI component includes determining alterations in microglia morphology.

5. The method of claim 1 wherein assessing the reference of neuro-inflammation includes a model of acute inflammation that increases measures of the ODI component with an increase in anisotropic diffusion in extracellular compartments.

6. The method of claim 1 wherein the report includes an image of the subject.

7. The method of claim 1 wherein the report includes an imaging biomarker map indicative of the quantified neuro-inflammation.

8. The method of claim 7 wherein the imaging biomarker map indicative of the quantified neuro-inflammation differentiates acute neuro-inflammation and chronic neuro-inflammation in the subject.

9. The method of claim 7 wherein the imaging biomarker map includes quantification information of the acute neuro-inflammation and the chronic neuro-inflammation in the subject.

10. The method of claim 1 further comprising quantifying both the acute neuro-inflammation and the chronic neuro-inflammation.

11. A method for non-invasively assessing neuro-inflammation in a subject, the method comprising:

acquiring neurite orientation dispersion and density imaging (NODDI) data of the subject;

processing the NODDI data to determine an orientation dispersion index (ODI) component of the NODDI data;

assessing the ODI component against one of a reference of neuro-inflammation or a prior ODI component acquired from the subject to determine an acute neuro-inflammation and chronic neuro-inflammation in the subject; and generating a report indicating the acute neuro-inflammation and the chronic neuro-inflammation in the subject.

12. The method of claim 11 wherein the reference of neuro-inflammation relates changes in ODI to changes in extracellular compartments in brain tissue.

13. The method of claim 12 wherein the changes in extracellular compartments include microglial cell density and morphology that are associated with neuro-inflammation.

14. The method of claim 11 wherein assessing the ODI component includes determining alterations in microglia morphology.

15. The method of claim 11 wherein assessing the reference of neuro-inflammation includes applying a model of acute inflammation that increases measures of the ODI component with an increase in anisotropic diffusion in extracellular compartments.

16. The method of claim 11 wherein assessing the ODI component includes quantifying the acute neuro-inflammation or chronic neuro-inflammation in the subject.

17. The method of claim 16 wherein the report includes an imaging biomarker map including quantified neuro-inflammation and distinguishing acute neuro-inflammation from chronic neuro-inflammation in the subject.

18. The method of claim 17 wherein the imaging biomarker map quantitatively displays acute neuro-inflammation and chronic neuro-inflammation in the subject.

19. The method of claim 11 further comprising quantifying both the acute neuro-inflammation and the chronic neuro-inflammation in the subject and including quantified acute neuro-inflammation and chronic neuro-inflammation in the report.

20. The method of claim 11 wherein the report includes longitudinal neuro-inflammation in the subject.

* * * * *